United States Patent
Pankratz et al.

(10) Patent No.: US 10,890,580 B2
(45) Date of Patent: Jan. 12, 2021

(54) REVERSIBLE CELL LABELLING WITH CONJUGATES HAVING TWO RELEASABLE BINDING SITES

(71) Applicant: Miltenyi Biotec GmbH, Bergisch Gladbach (DE)

(72) Inventors: Jennifer Pankratz, Cologne (DE); Christian Dose, Kürten (DE); Mario Assenmacher, Bergisch Gladbach (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 265 days.

(21) Appl. No.: 15/834,114

(22) Filed: Dec. 7, 2017

(65) Prior Publication Data

US 2018/0164296 A1 Jun. 14, 2018

(30) Foreign Application Priority Data

Dec. 13, 2016 (EP) ..................................... 16203607

(51) Int. Cl.
| | |
|---|---|
| *G01N 33/533* | (2006.01) |
| *G01N 33/536* | (2006.01) |
| *G01N 1/30* | (2006.01) |
| *G01N 33/569* | (2006.01) |
| *G01N 33/58* | (2006.01) |
| *G01N 33/532* | (2006.01) |

(52) U.S. Cl.
CPC ............ *G01N 33/533* (2013.01); *G01N 1/30* (2013.01); *G01N 33/532* (2013.01); *G01N 33/536* (2013.01); *G01N 33/569* (2013.01); *G01N 33/58* (2013.01); *G01N 2001/302* (2013.01)

(58) Field of Classification Search
CPC .. G01N 1/30; G01N 2001/302; G01N 33/532; G01N 33/533; G01N 33/536; G01N 33/569; G01N 33/58
See application file for complete search history.

(56) References Cited

U.S. PATENT DOCUMENTS

| | | | |
|---|---|---|---|
| 10,196,631 B2 * | 2/2019 | Brieden | G01N 33/54326 |
| 10,197,561 B2 * | 2/2019 | Dose | G01N 33/5306 |
| 2014/0113315 A1 * | 4/2014 | Brieden | G01N 33/532 |
| | | | 435/7.24 |
| 2015/0167064 A1 * | 6/2015 | Gao | C12Q 1/6804 |
| | | | 506/9 |
| 2016/0187326 A1 * | 6/2016 | Dose | G01N 33/5306 |
| | | | 435/7.24 |

OTHER PUBLICATIONS

Werther et al., "The use of the CELLection Kit™ in the isolation of carcinoma cells from mononuclear cell suspensions," J. Immunol. Methods, 2000, vol. 238, pp. 133-141.*

Cheal et al., "Evaluation of glycodendron and synthetically-modified dextran clearing agents for multi-step targeting of radio-isotopes for molecular imaging and radioimmunotherapy," Mol. Pharm., 2014, vol. 11, pp. 400-416; published online Nov. 23, 2013.*

* cited by examiner

*Primary Examiner* — Galina M. Yakovleva
(74) *Attorney, Agent, or Firm* — Jaquelin K. Spong

(57) ABSTRACT

The invention is directed to a Method for detecting a target moiety in a sample of biological specimens by:
a) providing at least one conjugate with the general formula (I)

$$A_n\text{-}P\text{-}B_m\text{-}C_q\text{-}X_o \qquad (I)$$

with
A: antigen recognizing moiety;
P: enzymatically degradable spacer;
B: first binding moiety
C second binding moiety
X: detection moiety;
n, m, q, o integers between 1 and 100,
wherein B and C are non-covalently bound to each other and A and B are covalently bound to P
b) labelling the target moiety recognized by the antigen recognizing moiety A with at least one conjugate
c) detecting the labelled target moiety via detecting moiety X
d) cleaving $C_q\text{-}X_o$ by disrupting the non-covalent bond between $B_m$ and $C_q$ from the labelled target moiety
e) cleaving the binding moiety $B_m$ from the labelled target moiety by enzymatically degrading spacer P.

The method is useful to identify target moieties on the biological specimens. The biological specimens detected by the conjugate can be subsequently removed from the sample.

3 Claims, 3 Drawing Sheets

REVERSIBLE CELL LABELLING WITH CONJUGATES HAVING TWO RELEASABLE BINDING SITES

CROSS REFERENCE TO RELATED APPLICATIONS

This US non-Provisional Patent Applications claims priority to EP 16203607.3, filed Dec. 13, 2016 and incorporated by reference in its entirety.

STATEMENT REGARDING FEDERALLY SPONSORED RESEARCH

Not applicable.

STATEMENT REGARDING MICROFICHE APPENDIX

Not applicable.

FIELD OF THE INVENTION

The present invention is directed to a process for detection of a target moiety in a sample of biological specimens.

BACKGROUND

Cell detection and separation techniques, e.g., magnetic cell separation, flow cytometry or flow sorting, are fundamental tools that contributed to the progress of biomedical research and cellular therapy in the past years. The techniques combine the specific labelling of a target moiety with conjugates having a detectable unit like a magnetic particle to retain and therefore isolate cells in a magnetic field, or like a fluorescent dye or transition metal isotope mass tag to detect and characterize cells by microscopy or cytometry. A technological challenge is still the release of the labelling after detection of the target moiety. Downstream applications like sequential sorting strategies, molecular diagnostic, or cell analysis can be prevented or affected by residual labelling.

Several reversible labelling systems were developed in the last years. One strategy exploits the specific competition of a non-covalent binding interaction. US20080255004 discloses a method for reversible binding to a solid support, e.g., magnetic particle, using antibodies recognizing the target moiety which are conjugated to modified biotin like desthiobiotin, and modified streptavidin or avidin bound to the solid support. The binding interaction of the modified binding partners is weaker compared to the strong and specific binding between biotin and streptavidin therefore facilitating the dissociation in the presence of these competitors. EP2725359 describes a system for reversible magnetic cell separation based on the non-covalent interaction of a ligand-PEO-Biotin-conjugate recognizing the target moiety and an anti-Biotin-antibody compromising a magnetic particle that can be released by adding the competing molecule biotin, streptavidin or an auxiliary reagent.

Beside these competitive release mechanism, the removal of labelling is mentioned by mechanical agitation, chemically cleavable or enzymatically degradable linkers. WO 96/31776 describes a method to release after separation magnetic particles from target cells by enzymatically cleaving a moiety of the particle coating, or a moiety present in the linkage group between the coating and the antigen recognizing moiety. An example is the application of magnetic particles coated with dextran and/or linked via dextran to the antigen recognizing moiety. Subsequent cleavage of the isolated target cells from the magnetic particle is initiated by the addition of the dextran-degrading enzyme dextranase. A related method in EP3037821 discloses the detection and separation of a target moiety according to, e.g. a fluorescence signal, with conjugates having an enzymatically-degradable spacer.

Recently the interest grew in techniques utilizing antigen recognizing moieties whose binding to the target moiety is characterized by a low-affinity constant. To ensure a specific and stable labelling with those low-affinity antigen recognizing moieties the structure of the labelling conjugate has to comprise a multimerization of the antigen recognizing moiety providing high avidity. Upon disruption of the multimerization the low-affinity antigen recognizing moiety can dissociate from the target moiety therefore providing the opportunity to release at its best the detection moiety and the antigen recognizing moiety from the target moiety.

This reversible multimer staining was first described in U.S. Pat. No. 7,776,562 respectively U.S. Pat. No. 8,298,782 wherein the multimerization is build up by a non-covalent binding interaction. Exemplary, low affinity peptide/MHC-monomers having a StreptagII are multimerized with streptactin and the multimerization is reversible upon addition of the competing molecule biotin.

The method was revised in U.S. Pat. No. 9,023,604 regarding the characteristics of the antigen recognizing moiety respectively receptor binding reagent to enable reversible labelling. Receptor binding reagents characterized by a dissociation rate constant about $0.5 \times 10^{-4}$ sec-1 or greater with a binding partner C are multimerized by a multimerization reagent with at least two binding sites Z interacting reversibly, non-covalently with the binding partner C to provide complexes with high avidity for the target antigen. The detectable label is bound to the multivalent binding complex. Reversibility of multimerization is initiated upon disruption of the binding between binding partner C and the binding site Z of the multimerization reagent. For example, in multimers of Fab-StreptagII/Streptactin, multimerization can be reversed by the competitor Biotin.

Multimerization strategies of these low-affinity antigen recognizing moieties based on the non-covalent binding interaction have the disadvantage to be dependent on the kinetic and thermodynamic characteristics of the non-covalent binding interaction. For specific labelling a preincubation of the reagents is required resulting in less defined and less reproducible conjugates with the risk of crosslinking and formation of aggregates. Alternatively labelling can be performed subsequently incubating first the antigen recognizing moiety in a temporarily monomeric labelling step and second the multimerization compound. However, if washing steps are performed to reduce the risk of unspecific binding interactions and high background signals a reduction of the labelling efficiency will result due to the fast dissociation characteristic of the monomer. This undesirable effect is shown in FIG. 2b) and example 3. Furthermore, those multimers are only applicable for single parameter not for multiple parameter labelling.

Beside the non-covalent multimerization strategy an embodiment of EP3037821 describes conjugates providing low-affinity antigen recognizing moieties and a detection moiety, e.g. fluorescent dye, covalently linked and therefore covalently multimerized via an enzymatically degradable spacer. The covalent linkage enables a stable and defined multimerization and the opportunity for multiple parameter labelling. During the enzymatic degradation of the spacer the detection moiety is released and the low-affinity antigen recognizing moiety is monomerized. An example of the embodiment is a Fab-Dextran-fluorochrome conjugate that can be applied for flow sorting of target cells.

SUMMARY

An object of the invention was a process for detection of a target moiety in a sample of biological specimens by labelling the target moiety with a conjugate having an antigen recognizing moiety and a detection moiety linked via an enzymatically degradable spacer and a non-covalent binding interaction, wherein after detecting or isolating the target moiety, the non-covalent binding interaction is disrupted, and the spacer is enzymatically degraded, thereby releasing the target cells from at least the detection moiety.

It was therefore an object of the invention to provide a method for specific labelling, detection and de-labelling of target moieties in a sample of biological specimen in order to enable further labelling, detection strategies.

It was found that conjugates enabling two release mechanisms, i.e. comprising an antigen binding moiety linked via an enzymatically degradable spacer and a non-covalent binding interaction between two binding moieties can be readily released from the target cells.

Object of the invention is therefore a method for detecting a target moiety in a sample of biological specimens by:
a) providing at least one conjugate with the general formula (I)

$$A_n\text{-}P\text{-}B_m\text{-}C_q\text{-}X_o \qquad (I)$$

with
A: antigen recognizing moiety;
P: enzymatically degradable spacer;
B: first binding moiety
C second binding moiety
X: detection moiety;
n, m, q, o integers between 1 and 100,
wherein B and C are non-covalently bound to each other and A and B are covalently bound to P
b) labelling the target moiety recognized by the antigen recognizing moiety A with at least one conjugate
c) detecting the labelled target moiety via detecting moiety X
d) cleaving $C_q\text{-}X_o$ by disrupting the non-covalent bond between $B_m$ and $C_q$ from the labelled target moiety
e) cleaving the binding moiety $B_m$ from the labelled target moiety by enzymatically degrading spacer P.

Compared to prior art technologies the present method enables new flexibility and control for the labelling and detection of a target moiety in a biological specimen.

The combination of two release mechanism enables control over release procedure allowing in sequential steps the release of the detection moiety and reversibility of the multimerization. Therefore, the method offers possibilities for new and flexible detection and isolation strategies, e.g. relabelling of the same target moiety and not only a similar target moiety with a different detection moiety after removal of the first detection moiety. Nevertheless, after the sequential or simultaneous removal via the two release mechanism at its best the complete conjugate with detection moiety and the antigen recognizing moiety is released form the target moiety.

The method of the invention may be utilized not only for detecting target moieties i.e. target cells expressing such target moieties, but also for isolating the target cells from a sample of biological specimens. The isolating procedures makes use of detecting the target moieties. For example, the detection of a target moiety by fluorescence may be used to trigger an appropriate separation process as performed on FACS or TYTO separation systems. In the method of the invention, the well-known magnetic cell separation process can also be used as detection and separation process, wherein the magnetic particles are detected by the magnetic field.

DETAILED DESCRIPTION

In the method of the invention, covalent and non-covalent bonds between the binding partners A, P, B, C and X may be disrupted by a variety of methods. For the purpose of the present invention, covalent bonds are defined as bonds between atoms sharing electron pairs or quasi-covalent bonds between non-covalent interaction partners with a dissociation constant of less than 10E-9 M. Non-covalent bonds are defined as bonds with a dissociation constant of greater than 10E-9 M.

The term "cleaving Cq-Xo by disrupting the non-covalent bond between Bm and Cq" means that the non-covalent bond between B and C is abrogated and the binding moiety Cq and detection moiety Xo are removed as fragment Cq-Xo for example by washing.

The term "cleaving the binding moiety Bm from the labelled target moiety by enzymatically degrading spacer P" means that covalent bonds of the fragment An-P-Bm are cleaved by degrading spacer P in a way that at least the binding moiety Bm are removed from the target moiety for example by dissociation or washing. In addition, the antigen recognizing moiety An might be removed.

The method of the invention may involve the removal of the recognizing moiety $A_n$ not only from the conjugate, but also from the target moiety. In this respect, the invention encompasses two embodiments by using conjugates with high-affinity (a) or low-affinity (b) antigen recognizing moieties A. A high-affinity antigen recognizing moiety A is capable of binding a target moiety in a 1:1 ratio, i.e. n=1 in formula (I). On the other hand, low-affinity antigen recognizing moieties are not capable of binding a target moiety in a 1:1 ratio, but several low-affinity antigen recognizing moieties in one conjugate are needed to bind to the target moiety, i.e. n>1 in formula (I).

Figure 1:
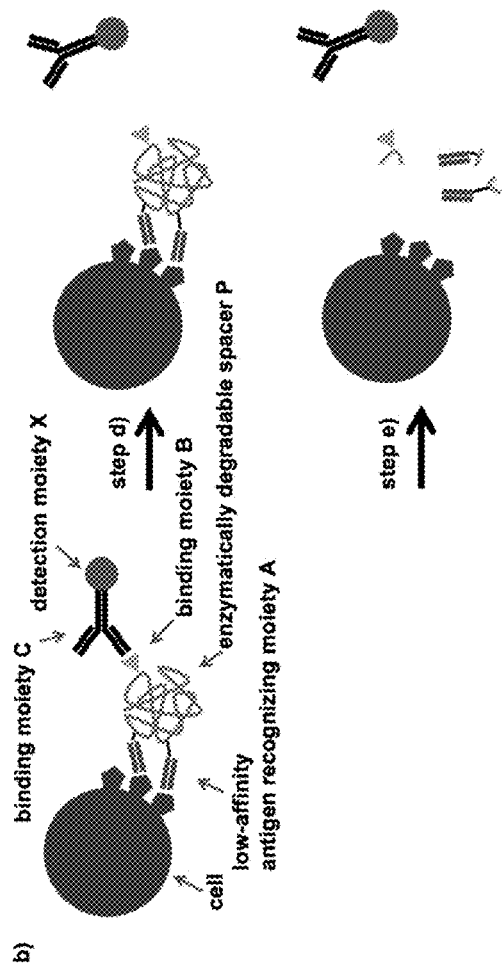
FIG. 1 shows schematically the method of the invention by specific labelling and release of a target cell as biological specimen with a conjugate of low-affinity (b) antigen recognizing moiety A, enzymatically degradable spacer P, binding moiety B and C and detection moiety X.

FIG. 1 shows schematically an embodiment of the invention by specific labelling of a target moiety on a target cell as biological specimen with a conjugate of low-affinity (b) antigen recognizing moiety A, enzymatically degradable spacer P, the binding moieties B and C and detection moiety X. In this embodiment, the detection moiety X and binding moiety C is released from the target moiety after disrupting the non-covalent binding interaction between the binding moieties B and C. When the spacer P is enzymatically degraded, low-affinity antigen recognizing moieties A will be monomerized during the enzymatically degradation of spacer P. As monomers, low-affinity antigen recognizing moieties A are not capable of providing a stable bond to the target moiety and will dissociate from the target moiety. Accordingly, low-affinity antigen recognizing moiety are removed from the target moiety, the detection moiety X, the binding moieties B and C, the spacer P and the antigen recognizing moiety A, leaving untouched target cells.

The process of the invention may be performed in one or more sequences of the steps a) to e). After each sequence, the detection moiety and optionally the antigen recognizing moiety is released (removed) from the target moiety. Especially when the biological specimens are living cells which shall be further processed, the method of the invention has the advantage of providing unlabelled cells.

After and/or before each step a)-e) one or more washing steps can be performed to remove unwanted material like unbound conjugate (I) or released parts of the conjugate like the binding moiety C and detection moiety X or antigen recognizing moiety A or reagents used for disruption. The term "washing" means that the sample of biological specimen is separated from the environmental buffer by a suitable procedure, e.g., sedimentation, centrifugation, draining or filtration. Before this separation washing buffer can be added and optionally incubated for a period of time. After this separation, the sample can be filled or resuspended again with buffer.

Target Moiety

The target moiety to be detected with the method of the invention can be on any biological specimen, like tissues slices, cell aggregates, suspension cells, or adherent cells. The cells may be living or dead. Preferable, target moieties are antigens expressed intracellular or extracellular on biological specimen like whole animals, organs, tissues slices, cell aggregates, or single cells of invertebrates, (e.g., *Caenorhabditis elegans, Drosophila melanogaster*), vertebrates (e.g., *Danio rerio, Xenopus laevis*) and mammalians (e.g., *Mus musculus, Homo sapiens*).

Detection Moiety

The detection moiety X of the conjugate may be any moiety possessing a property or function which can be used for detection purposes of cells. Preferable, detection moiety X is selected from the group consisting of chromophore moiety, fluorescent moiety, phosphorescent moiety, luminescent moiety, light absorbing moiety, radioactive moiety, transition metal and isotope mass tag moiety, solid support with shape of particles, for example, sheets, plates, membranes, tubes, columns, wells, or micro arrays, magnetic particle.

Suitable fluorescent moieties are those known from the art of immunofluorescence technologies, e.g., flow cytometry or fluorescence microscopy. In these embodiments of the invention, the target moiety labelled with the conjugate is detected by exciting the detection moiety X and detecting the resulting emission (photoluminescence). In this embodiment, the detection moiety X is preferable a fluorescent moiety.

Useful fluorescent moieties might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyrromethenes, or metallo-organic complexes, such as Ru, Eu, Pt complexes. Besides single molecule entities, clusters of fluorescent proteins or small organic molecule dyes, as well as nanoparticles, such as quantum dots, upconverting nanoparticles, gold nanoparticles, dyed polymer nanoparticles can also be used as fluorescent moieties.

Another group of photo luminescent detection moieties are phosphorescent moieties with time-delayed emission of light after excitation. Phosphorescent moieties include metallo-organic complexes, such as Pd, Pt, Tb, Eu complexes, or nanoparticles with incorporated phosphorescent pigments such as lanthanide doped $SrAl_2O_4$.

In another embodiment of the invention the target labeled with the conjugate is detected without prior excitation by irradiation. In this embodiment the detection moiety can be a radioactive label. They may be in the form of radioisotope labelling by exchanging non-radioactive isotopes for their radioactive counterparts, such as tritium, $^{32}P$, $^{35}S$ or $^{14}C$, or introducing covalently bound labels, such as $^{125}I$, which is bound to tyrosine, $^{18}F$ within fluorodeoxyglucose, or metallo-organic complexes, i.e. $^{99}Tc$-DTPA.

In another embodiment the detection moiety is capable of causing chemo luminescence, i.e. horseradish peroxidase label in the presence of luminol.

In another embodiment of the invention the target labeled with the conjugate is not detected by radiation emission, but by absorption of UV, visible light, or NIR radiation. Suitable light-absorbing detection moieties are light absorbing dyes without fluorescence emission, such as small organic molecule quencher dyes like N-aryl rhodamines, azo dyes, and stilbenes.

In another embodiment, the light-absorbing detection moieties X can be irradiated by pulsed laser light, generating a photoacoustic signal.

In another embodiment of the invention the target labeled with the conjugate is detected by mass spectrometric detection of a transition metal isotope. Transition metal isotope mass tag labels might be introduced as covalently bound metallo-organic complexes or nanoparticle component. Known in the art are isotope tags of lanthanides and adjacent late transition elements.

Furthermore, the detection moiety X can be a solid support possessing a property or function which can be used for detection purposes of cells. Suitable solid supports are known in biotechnology for immobilizing cells and can have the shape of particles, for example, sheets, plates, membranes, tubes, columns, wells, or micro arrays manufactured from various materials like polystyrene (PS), polymethylmethacrylate (PMMA), polyvinyl toluene (PVT), polyethylene (PE), or polypropylene (PP). Suitable materials are commercially available.

The solid support can further be a magnetic particle, also known in the art as nano- to microscale magnetic bead. The mean diameter of the beads can range from 10 nm to 10 µm. Biocompatible magnetic particles are commercially available and consist of, for example, forms of magnetically iron oxide coated by a shell of dextran molecules or silica. The solid support may also be polymers containing magnetic materials. Suitable particles are commercial available from Miltenyi Biotec GmbH, Germany under the trade name "MicroBeads" and "MACSiBeads" possessing a hydrodynamic diameter of 50-100 nm or 3-4 lam, respectively.

The detection moiety X can be covalently or non-covalently coupled to the binding moiety C. Methods for covalently or non-covalently conjugation is known by persons skilled in the art. In case of a covalent bond between the detection moiety X and the binding moiety C, a direct reaction of an activated group either on the detection moiety X or on the binding moiety C with a functional group on either the binding moiety C or on the detection moiety X or via a heterobifunctional linker molecule, which is firstly reacted with one and secondly reacted with the other coupling partner is possible.

For example, a large number of heterobifunctional compounds are available for linking to entities. Illustrative entities include: azido benzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-y-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, succinimidyl-[(N-maleimidopropionamido) polyethyleneglycol] esters (NHS-PEG-MAL), and succinimidyl 4-[N-maleimidomethyl]cyclohexane-1-carboxylate. A preferred linking group is 3-(2-pyridyldithio)propionic acid N-hydroxysuccinimide ester (SPDP), or 4-(N-maleimidomethyl)-cyclohexane-1-carboxylic acid N-hydroxysuccinimide ester (SMCC).

A quasi-covalent binding of the detection moiety X to the binding moiety C can be achieved with binding systems providing a dissociation constant of 10-9 M, e.g., Biotin-Avidin binding interaction.

The conjugate used in the method of the invention may comprise 1 to 100, preferable 1-20 detection moieties X.

First and Second Binding Moieties B and C

Binding moiety B and binding moiety C are binding partners able to bind non-covalently and reversibly to each other. For the purpose of the present invention, non-covalent and reversible bonds are defined as bonds with a dissociation constant of greater than 10E-9 M.

Binding moiety B, respectively C may be biotin, a derivative or analogue thereof like iminobiotin, desthiobiotin, diaminobiotin, HABA (2-(4'-hydroxyphenylazo)benzoic acid); biotin peptide analogues like streptagI (AWRHPQFGG) or streptagII (WSHPQFEK). The biotin, a derivative or analogue thereof may be separated from the detection moiety X or enzymatically degradable spacer P by a spacer group consisting of, e.g., polyethylene glycol (PEO) or aminocaprolic acid (so called "LC"). Corresponding binding partners and therefore binding moiety C, respectively B, may be streptavidin or avidin or analogues thereof like nitro-streptavidin or mutated variants, e.g. strep-tactin or monomeric streptavidin; antibodies like anti-Biotin-antibody or anti-Strep-tag II antibody.

Furthermore, binding moiety B may be a biotin derivate having a spacer group consisting of polyethylene glycol with 1 to 500 repeating units.

Alternative binding moieties are known from literature like oligohistidine-tag and anti-His-antibodies or Ni-NTA; FLAG-peptide and anti-FLAG antibody; calmodulin-binding peptide and calmodulin in the presence of divalent cations; polymer and anti-polymer-antibodies like polythyleneglycol and anti-polythyleneglycol-antibody; hybridizing Oligonucleotides; maltose-binding-protein-tag and maltose-binding-protein.

The binding moiety B can be covalently coupled to the enzymatically degradable spacer P. Methods for the conjugation are known by persons skilled in the art and the same as mentioned for the detection moiety X to the binding molecule C. Depending on the structure and functional groups of the binding moieties conjugation may take place directly or after modification to enable the specific linkage. Spacer groups, e.g., alkyl chains or polyethylene glycol, may be inserted providing a certain distance between the binding moiety B or C to the enzymatically degradable spacer P and detection moiety X.

The conjugate used in the method of the invention may comprise 1 to 100, preferable 1-20 binding moieties B and C.

Disruption of the Non-Covalent Bond Between the Binding Moieties B and C

The non-covalent bond between B and C is reversible and therefore can be disrupted by the addition of competing molecules as release reagent capable of binding to one of the binding moieties B and C displacing the respective moiety. Regarding the exemplary mentioned binding moieties in "B and C as binding moieties" competing molecules may be biotin or streptavidin; peptides like polyhistidine, FLAG-peptide, calmodulin-binding peptide; small molecules like imidazole or maltose; chelators like EDTA; polymers like polyethylene glycol; complementary oligonucleotides.

The efficiency of the competing reaction is dependent on the thermodynamic and kinetic characteristic of the interaction between the binding moieties B and C and the competing molecule, the concentration of the components, the environmental conditions like temperature and the reaction time. The specific conditions have to be evaluated according to the desired efficiency.

In a variant of the invention the competing molecule displacing the binding moiety C may be conjugated to a different detection moiety X therefore enabling during disruption an exchange of the detection moiety.

Furthermore, the disruption may be achieved by the initiation of conformational changes lowering the strength of the binding interaction between the binding moieties B and C, e.g., chelating divalent cation bound in calmodulin inducing conformational change.

Beside this, the bond between B and C may be cleaved by mechanical agitation inducing shear forces or by changing environmental conditions like pH, temperature or salt concentrations influencing the binding interaction.

It is possible to combine more than one method for disruption.

Usually the efficiency of the cleavage induces a reduction of the labelling with the C-X of at least about 80%, more usually of at least about 95%, preferably of at least about 99%. The conditions for release may be empirically optimized in terms of temperature, pH, etc. The disruption will usually be completed in at least about 15 minutes, more usually at least about 10 minutes, and will usually not be longer than about 2 h.

Enzymatically Degradable Spacer P

The enzymatically degradable spacer P can be any molecule which can be cleaved by a specific enzyme like a hydrolase. Suitable as enzymatically degradable spacer P are, for example, polysaccharides, proteins, peptides, depsipeptides, polyesters, nucleic acids, and derivatives thereof.

Suitable polysaccharides are, for example, dextrans, pullulans, inulins, amylose, cellulose, hemicelluloses, such as xylan or glucomannan, pectin, chitosan, or chitin, which may be derivatized to provide functional groups for covalent or non-covalent binding of the binding moiety B and the antigen recognizing moiety A. A variety of such modifications are known in the art, for example, imidazolyl carbamate groups may be introduced by reacting the polysaccharide with N,N'-carbonyl diimidazole. Subsequently amino groups may be introduced by reacting said imidazolyl carbamate groups with hexane diamine Polysaccharides may also be oxidized using periodate to provide aldehyde groups or with N,N'-dicyclohexylcarbodiimide and dimethylsulfoxide to provide ketone groups. Aldehyde or ketone functional groups can be reacted subsequently preferably under conditions of reductive amination either with diamines to provide amino groups or directly with amino substituents on a proteinaceous binding moiety. Carboxymethyl groups may be introduced by treating the polysaccharide with chloroacetic acid. Activating the carboxy groups with methods known in the art which yield activated esters such N-hydroxysuccinimid ester or tetrafluorophenyl ester allows for reaction with amino groups either of a diamine to provide amino groups or directly with an amino group of a proteinaceous binding moiety. It is generally possible to introduce functional group bearing alkyl groups by treating polysaccharides with halogen compounds under alkaline conditions. For example, allyl groups can be introduced by using allyl bromide. Allyl groups can further be used in a thiol-ene reaction with thiol bearing compounds such as cysteamine to introduce amino groups or directly with a proteinaceous binding moiety with thiol groups liberated by reduction of disulfide bonds or introduced by thiolation for instance with 2-iminothiolane.

Proteins, peptides, and depsipeptides used as enzymatically degradable spacer P can be functionalized via side chain functional groups of amino acids to attach binding moiety B and antigen recognizing moiety A. Side chains functional groups suitable for modification are for instance amino groups provided by lysine or thiol groups provided by cysteine after reduction of disulfide bridges.

Polyesters and polyesteramides used as enzymatically degradable spacer P can either be synthesized with comonomers, which provide side chain functionality or be subsequently functionalized. In the case of branched polyesters functionalization can be via the carboxyl or hydroxyl end groups. Post polymerization functionalization of the polymer chain can be, for example, via addition to unsaturated bonds, i.e. thiolene reactions or azide-alkine reactions, or via introduction of functional groups by radical reactions.

Nucleic acids used as enzymatically degradable spacer P are preferably synthesized with functional groups at the 3' and 5' termini suitable for attachment of the binding moiety B and antigen recognizing moiety A. Suitable phosphoramidite building blocks for nucleic acid synthesis providing for instance amino or thiol functionalities are known in the art.

The enzymatically degradable spacer P can be composed of more than one different enzymatically degradable units, which are degradable by the same or different enzyme.

Enzymes for Degrading Spacer P

The enzymatically degradable spacer P is degraded by the addition of an appropriate enzyme. The choice of enzyme as release reagent is determined by the chemical nature of the enzymatically degradable spacer P and can be one or a mixture of different enzymes.

Enzymes are preferably hydrolases, but lyases or reductases are also possible. Preferable enzymes may be is selected from the group consisting of glycosidases, dextranases, pullulanases, amylases, inulinases, cellulases, hemicellulases, pectinases, chitosanases, chitinases, proteinases, esterases, lipases, and nucleases.

For example, if the spacer P is a polysaccharide, glycosidases (EC 3.2.1) are most suitable as release agents. Preferred are glycosidases that recognize specific glycosidic structures, e.g., dextranase (EC3.2.1.11), which cleaves at the $\alpha(1\rightarrow6)$ linkage of dextrans, pullulanases, which cleave either $\alpha(1\rightarrow6)$ linkages (EC 3.2.1.142) or $\alpha(1\rightarrow6)$ and $\alpha(1\rightarrow4)$ linkages (EC 3.2.1.41) of pullulans, neopullulanase (EC 3.2.1.135), and isopullulanase (EC 3.2.1.57), which cleave $\alpha(1\rightarrow4)$ linkages in pullulans. $\alpha$-Amylase (EC 3.2.1.1), and maltogenic amylase (EC 3.2.1.133), which cleave $\alpha(1\rightarrow4)$ linkages in amylose, inulinase (EC 3.2.1.7), which cleaves $\beta(2\rightarrow1)$ fructosidic linkages in inulin, cellulase (EC 3.2.1.4), which cleaves at the $\beta(1\rightarrow4)$ linkage of cellulose, xylanase (EC 3.2.1.8), which cleaves at the $\beta(1\rightarrow4)$ linkages of xylan, pectinases such as endo-pectin lyase (EC 4.2.2.10), which cleaves eliminative at the $\alpha(1\rightarrow4)$ D-galacturonan methyl ester linkages, or polygalacturonase (EC 3.2.1.15), which cleaves at the $\alpha(1\rightarrow4)$ D-galactosiduronic linkages of pectin, chitosanase (EC 3.2.1.132), which cleaves at the $\beta(1\rightarrow4)$ linkages of chitosan and endo-chitinase (EC 3.2.1.14) for cleaving of chitin.

Proteins and peptides may be cleaved by proteinases, which need to be sequence specific to avoid degradation of target structures on cells. Sequence specific proteases are for instance TEV protease (EC 3.4.22.44), which is a cysteine protease cleaving at the sequence ENLYFQ\S, enteropeptidase (EC 3.4.21.9), which is a serine protease cleaving after the sequence DDDDK, factor Xa (EC 3.4.21.6), which is a serine endopeptidase cleaving after the sequences IEGR or IDGR, or HRV3C protease (EC3.4.22.28), which is a cysteine protease cleaving at the sequence LEVLFQ\GP.

Depsipeptides, which are peptides containing ester bonds in the peptide backbone, or polyesters may be cleaved by esterases, such as porcine liver esterase (EC 3.1.1.1) or porcine pancreatic lipase (EC 3.1.1.3). Nucleic acids may be cleaved by endonucleases, which can be sequence specific, such as restriction enzymes (EC 3.1.21.3, EC 3.1.21.4, EC 3.1.21.5), such as EcoRI, HindII or BamHI or more general such as DNAse I (EC 3.1.21.1), which cleaves phosphodiester linkages adjacent to a pyrimidine.

The amount of enzyme added needs to be sufficient to degrade substantially the spacer in the desired period of time. Usually the efficiency is at least about 80%, more usually at least about 95%, preferably at least about 99%. The conditions for release may be empirically optimized in terms of temperature, pH, presence of metal cofactors, reducing agents, etc. The degradation will usually be completed in at least about 15 minutes, more usually at least about 10 minutes, and will usually not be longer than about 2 h.

It is not necessary to degrade spacer P entirely. For the method of the invention, it is necessary to degrade spacer P as much that binding moiety B and/or antigen recognizing moiety A can be removed from the labeled target moiety by washing or dissociation.

Antigen Recognizing Moiety A

The term "antigen recognizing moiety A" refers to any kind of antibody, fragmented antibody or fragmented antibody derivatives, directed against the target moieties expressed on the biological specimens, like antigens expressed intracellular or extracellular on cells. The term relates to an antibody, a fragmented antibody, a fragmented antibody derivative, peptide/MHC-complexes targeting TCR molecules, cell adhesion receptor molecules, receptors for costimulatory molecules or artificial engineered binding molecules. Fragmented antibody derivatives, are for example Fab, Fab', F(ab')2, sdAb, scFv, di-scFv, nanobodies. Such fragmented antibody derivatives may be synthesized by recombinant procedures including covalent and non-covalent conjugates containing these kind of molecules. Further examples of antigen recognizing moieties are peptide/MHC-complexes targeting TCR molecules, cell adhesion receptor molecules, receptors for costimulatory molecules, artificial engineered binding molecules, e.g., peptides or aptamers which target, e.g., cell surface molecules.

The conjugate used in the method of the invention may comprise 1 to 100, preferable 1 to 20 antigen recognizing moieties A. The interaction of the antigen recognizing moiety with the target moiety can be of high or low affinity. Binding interactions of a single low-affinity antigen recognizing moiety is too low to provide a stable bond with the antigen. Low-affinity antigen recognizing moieties can be multimerized by conjugation to the enzymatically degradable spacer P to furnish high avidity.

Preferable, the term "Antigen recognizing moiety A" refers to an antibody directed against antigen expressed by the biological specimens (target cells) intracellular, like IL2, FoxP3, CD154, or extracellular, like CD3, CD14, CD4, CD8, CD25, CD34, CD56, and CD133.

The antigen recognizing moieties A, especially antibodies, can be coupled to the spacer P through side chain amino or sulfhydryl groups. In some cases, the glyosidic side chain of the antibody can be oxidized by periodate resulting in aldehyde functional groups.

The antigen recognizing moiety A can be covalently or non-covalently coupled to the spacer P. Methods for covalent or non-covalent conjugation are known by persons skilled in the art and the same as mentioned for conjugation of the detection moiety X.

The method of the invention is especially useful for detection and/or isolation of specific cell types from complex mixtures and may comprise more than one sequential or parallel sequences of the steps a)-e). The method may use a variety of combinations of conjugates. For example, a conjugate may comprise antibodies specific for two different epitopes, like two different anti-CD34 antibodies. Different antigens may be addressed with different conjugates comprising different antibodies, for example, anti-CD4 and anti-CD8 for differentiation between two distinct T-cell-populations or anti-CD4 and anti-CD25 for determination of different cell subpopulations like regulatory T-cells.

Variants of the Method

The method of the invention provides a high flexibility for the specific labeling with the conjugate and release of the conjugate providing a plurality of different detection strategies.

Any step can be monitored qualitatively or quantitatively according to the detection moieties $X_o$ used or by other applicable quantitative or qualitative methods known by persons skilled in the art, e.g., by visual counting. This can be useful to determine the efficiency of the individual steps provided by the method of the invention. Furthermore, it is possible to label the sample of biological specimen in or after any of the steps a)-e) for qualitatively or quantitatively monitoring. Such methods for labeling are known by persons skilled in the art, like utilizing non-degradable conjugates according to general formula (II) to (V) as explained in the following.

Step a

In step a) of the method, at least one conjugate with the general formula (I) $A_n$-P-$B_m$-$C_q$-$X_o$ (I) is provided. In order to detect different target moieties or the same target moiety by different detection moieties, different conjugates having the general formula (I) $A_n$-P-$B_m$-$C_q$-$X_o$ can be provided, wherein the conjugates and its components, A, P, B, C, X, n, m, q, o have the same meaning, but can be the same or different kind and/or amount of antigen recognizing moiety A and/or enzymatically degradable spacer P and/or binding moiety B and/or binding moiety C and/or detection moiety X.

It is furthermore possible to provide in addition to conjugates with the general formula (I) $A_n$-P-$B_m$-$C_q$-$X_o$ further conjugates which survive at least one of the cleaving steps d) and/or e) and which can be used for further detection.

Such further conjugates may have the general formula (II) An-P'-B'm-C'q-Xo with A, X, n, m, q, o having the same chemical meaning as in formula (I) but wherein A and B' are covalently bound to P' and/or C' is covalently bound to X and/or wherein P' is a spacer which is not enzymatically degradable and/or wherein B' binds covalently to C'.

In another variant, additionally at least one non-enzymatically degradable conjugate with the general formula (III) $A_n$-$B_m$-$C_q$-$X_o$, wherein A, B, C, X, n, m, q, o have the same meaning as in formula (I) can be provided.

Furthermore, it is possible to provide at least one conjugate with the general formula (IV) $A_n$-P-$X_o$, wherein A, P, X, n, o has the same meaning as in formula (I).

Additionally, at least one conjugate with the general formula (V) $A_n$-$X_o$, wherein A, X, n, o has the same meaning as in formula (I) can be provided.

Conjugates with the general formula (II)-(V) survive at least one of the cleaving steps d) and/or e) and can be used for further detection.

Step b

In step b), the target moiety of the sample of biological specimens is labelled with the conjugate.

In a first embodiment of step b), labelling the target moiety with the conjugate is performed by first labelling the target moiety with a first conjugate An-P-Bm and second labelling the first labelled target moiety with a second conjugate Cq-Xo. In the following, this embodiment is referred to as "i)". In a variant of this embodiment, between the first and second labelling, a washing step is performed in order to reduce the amount of unbound An-P-Bm before the second incubation. An example of this procedure is shown in FIG. 2a) and example 3. Furthermore, after cleaving Cq-Xo from the labelled target moiety in step d) the target moiety labelled with An-P-Bm is labelled with a second conjugate Cq-Xo.

In a second embodiment of step b), the target moiety is labelled with the conjugate $A_n$-P-$B_m$-$C_q$-$X_o$ directly, i.e. the assembly of the conjugate is performed before contacting with the target moiety recognized by the antigen recognizing moiety A. In the following, this embodiment is referred to as "ii)".

The embodiments i) and ii) of step b) may be performed in several variants.

In a variant of the invention the contacting with more than one conjugate of the general formula (I) can proceed in any combination of i) and ii). For example, more than one conjugate can be incubated simultaneously in i) or ii) or subsequently in more than one step i) or ii), or one conjugate may be incubated according to i) and another according to ii).

Furthermore, conjugates not recognized by a target moiety can be removed by washing for example with buffer before the target moiety labeled with the conjugate is detected or isolated in step c) or before a next contacting step b).

In a variant of the invention, it is possible to perform multiple steps b) or perform step b) with at least one conjugate of the general formula (I) in addition with at least one conjugate of the general formula (II)-(V).

Conditions during incubation are known by persons skilled in the art and may be empirically optimized in terms of time, temperature, pH, etc. Usually incubation time is up to 1 h, more usually up to 30 min and preferred up to 15 min. Temperature is usually 4-37° C., more usually less than 37° C.

Step c

The method and equipment to detect the target moiety labeled with the conjugate $A_n$-P-$B_m$-$C_q$-$X_o$ in c) is determined by the detection moiety X.

The method of the invention may be utilized not only for detecting target moieties i.e. target cells expressing such target moieties, but also for isolating the target cells from a sample of biological specimens according to the detection moiety X. In the method of the invention the term "detection" encompasses "isolation".

For example, the detection of a target moiety by fluorescence may be used to trigger an appropriate separation process as performed on FACS or TYTO separation systems. In the method of the invention, the well-known magnetic cell separation process can also be used as detection and isolation process, wherein the magnetic particles are detected by the magnetic field.

In one variant of the invention, the detection moiety X is a fluorescent moiety. Targets labeled with fluorochrome-conjugate are detected by exciting the fluorescent moiety X and analyzing the resulting fluorescence signal. The wavelength of the excitation is usually selected according to the absorption maximum of the fluorescent moiety X and provided by LASER or LED sources as known in the art. If several different detection moieties X are used for multiple color/parameter detection, care should be taken to select fluorescent moieties having not overlapping absorption spectra, at least not overlapping absorption maxima. In case of a fluorescent moieties as detection moiety the targets may be detected, e.g., under a fluorescence microscope, in a flow cytometer, a spectrofluorometer, or a fluorescence scanner. Light emitted by chemoluminescence can be detected by similar instrumentation omitting the excitation.

In another variant of the invention the detection moiety is a light absorbing moiety, which is detected by the difference between the irradiation light intensity and the transmitted or reflected light intensity. Light absorbing moieties might also be detected by photoacoustic imaging, which uses the absorption of a pulsed laser beam to generate an acoustic like an ultrasonic signal.

Radioactive detection moieties are detected though the radiation emitted by the radioactive isotopes. Suitable instrumentation for detection of radioactive radiation include, for example, scintillation counters. In case of beta emission electron microscopy can also be used for detection.

Transition metal isotope mass tag moieties are detected by mass spectrometric methods such as ICP-MS, which is integrated in mass cytometry instrumentation.

In a further variant of the invention the detection moiety is a solid support. Depending on the size and density those might be detected by visual inspection or in a microscope.

Magnetic particles are detected magnetically, e.g., by magnetic relaxometry, magnetic resonance imaging (MRI), magnetic force microscopy (MFM), superconducting quantum interference devices (SQUIDs), magnetometer.

The target moiety can be isolated according to their detection signal by optical means, electrostatic forces, piezoelectric forces, mechanical separation, acoustic means or magnetic forces.

In one variant of the invention, suitable for such separations according to a fluorescence signal are especially flow sorters, e.g., FACS or MEMS-based cell sorter systems, for example as disclosed in EP14187215.0 or EP14187214.3.

In another variant, wherein the detection moiety is a solid support the isolation may be performed by mechanical trapping of the solid support, e.g., in a column or a sieve, or according to their density, e.g. by sedimentation or centrifugation.

Furthermore, target moieties labelled with a magnetic particle may be isolated by applying a magnetic field. Magnetic cell sorting is known to the person skilled in the art and can be conducted in a permanent or an electromagnetic field with or without the use of a ferromagnetic column containing ferromagnetic material. Columns containing ferromagnetic material enhance the gradient of the magnetic field and are available from Miltenyi Biotec GmbH, Germany.

In further variants of the invention it is possible to combine at least one detection and/or isolation step c) simultaneous or in subsequent steps.

Furthermore, during or after isolation of the target moieties contaminating non-labelled moieties of the sample of biological specimen can be removed by washing for example with buffer.

Step d

After detection step c), the non-covalent bond between $B_m$ and $C_q$ is disrupted in step d), thereby cleaving the binding moiety $C_q$ and detection moiety $X_o$ from the conjugate (I).

Disrupting the non-covalent bond between Bm and Cq in step d) may be performed by adding a release agent that binds to the first binding moiety B, thereby displacing the second binding moiety C and/or by adding a release agent that binds to the second binding moiety C, thereby displacing the first binding moiety B.

In a variant of the invention, this disruption step can be performed outside the detection system, e.g., in a solution of the target moiety. For example, target moieties labelled with a fluorescent or light absorbing moiety are incubated for disruption in a tube, or target moieties labelled with magnetic particles may be washed from the separation column and get the magnetic label removed outside of the magnetic field.

In another variant, the disruption step can implemented in the detection setup. For example, the disruption may take place during the detection of the signal, e.g., during fluorescence microscopy, cytometry, photometry or MRI. The reduction of the detection signal might therefore be monitored in real time. In another example the disruption may also take place within the magnetic field. The magnetically labeled target moiety can be unlabeled by adding, e.g. the competing molecule, to the column located in the magnetic field. In this variant, the target moieties are eluted from the column/the magnetic fields whereas the magnetic label remains on the column and in the magnetic field.

Optionally after disruption in d) there can be another step c) with detecting or isolating the target moiety.

The binding moiety C and detection moiety X and/or residual target moieties still labelled with the conjugate (I) or non-cleaved parts of conjugate (I) and/or the reagent used for disruption in d) can be separated from the sample. This kind of isolation step can be performed by a washing step or by utilizing the methods described in step c) detection and/or isolation. The separation can be achieved by mechanical trapping of the solid support, e.g., in a column or a sieve. Furthermore, magnetic particles as solid support can be removed by applying a magnetic field as already described for isolation of target moieties. Using ferromagnetic columns, this is preferable conducted in at least one (the same) or especially in two different columns containing ferromagnetic material.

The one or more optionally detection and/or isolation steps provide a possibility to separate the released target moiety or determine the efficiency of the disruption step d).

Step e

After disruption of non-covalent bond between Bm and Cq in step d), in step e), binding moiety Bm is cleaved from the labelled target moiety by enzymatically degrading spacer P, i.e. the covalent bonds within An-P-Bm are disrupted.

The disruption can be performed outside of the detection system, e.g., in a solution of the target moiety in a tube.

Depending on the antigen recognizing moiety A, when the spacer P is enzymatically cleaved, the low-affinity antigen recognizing moieties will be monomerized and may dissociate which results in a complete removal of the detection moiety X, the spacer P, the binding moieties B and C and the antigen recognizing moiety A after step d)+e). High-affinity antigen recognizing moieties provide a stable bond which results in a removal of the detection moiety X, the spacer P and the binding moieties B and C after step d)+e).

Optionally after disruption in e) there can be another step c) with detecting or isolating the target moiety.

The binding moiety B and/or the enzymatically degraded spacer P and/or antigen recognizing moiety A and/or the reagent used for disruption in e) can be separated from the sample by, e.g., washing.

In a variant of the invention the disruption steps d) and e) can be performed simultaneously. Therefore, the disruption can take place outside of the detection system or implemented in the detection setup as described in step d) disruption.

The binding moiety C and detection moiety X and/or the enzymatically degraded spacer P and/or binding moiety B and/or antigen recognizing moiety A and/or residual target moieties still labelled with the conjugate (I) or non-cleaved parts of conjugate (I) and/or the reagent used for disruption in d) and/or e) can be separated from the sample. This kind of isolation step can be performed by a washing step or by utilizing the methods described in step c) detection and/or isolation. The separation can be achieved by mechanical trapping of the solid support, e.g., in a column or a sieve. Furthermore, magnetic particles as solid support can be removed by applying a magnetic field as already described for isolation of target moieties. Using ferromagnetic columns, this is preferable conducted in at least one (the same) or especially in two different columns containing ferromagnetic material.

Those one or more optionally detection and/or isolation steps provide a possibility to separate the released target moiety or determine the efficiency of the disruption step e) or d)+e).

Sequences of Steps a) to e)

The method of the invention may be performed in one or more sequences of the steps a) to e). After each sequence, the detection moiety and optionally the antigen recognizing moiety is released (removed) from the target moiety. Furthermore, sequences with combinations of any of the steps a) to e) are possible.

The method of the invention can be performed in the following embodiments:

Embodiment A of the invention is characterized in that steps a) to e) are performed in at least two subsequent sequences, wherein in each sequence conjugates An-P-Bm-Cq-Xo (I) are used having different detection moieties X.

In this embodiment, the sample of biological specimens is contacted in a first step b) with a first conjugate $A_n$-P-$B_m$-$C_q$-$X1_o$, performing the detection in step c), cleaving the conjugate in subsequent or simultaneous steps d) and e). The sample of biological specimens (depending on A still labelled with A) is contacted in a next sequence with a second conjugate $A_n$-P-$B_m$-$C_q$-$X2_o$, the detection is performed, and the conjugate cleaved in subsequent or simultaneous steps step d) and e). A, P, B, C are the same kind; n, m, q, o can be the same or different amount. This variant can be extended with further conjugates providing different X. An example for this variant is the magnetic labelling and isolation of a target cell population out of a sample of biological specimen followed by fluorescent labelling enabling flow cytometry or microscopy analysis or a fluorescent based flow sorting for further purification. In this variant the labelling efficiency in the second step can be reduced due to residual labelling with A after the first sequence.

Embodiment B of the invention is characterized in that step a) at least two conjugates An-P-Bm-Cq-Xo having different detection moieties X are provided and in at least two steps c) the labelled target moieties are detected via the different detection moieties X.

In this embodiment, the sample of biological specimens is contacted in step b) with a first conjugate $A_n$-P-$B_m$-$C_q$-$X1_o$ and a second conjugate $A_n$-P-$B_m$-$C_q$-$X2_o$, performing the detection in two subsequent step c), cleaving both conjugates simultaneously in subsequent or simultaneous steps d) and e). A, P, B, C are the same kind; n, m, q, o can be the same or different amount. This variant can be extended with further conjugates providing different X. An example for this variant is the magnetic and fluorescent labelling and isolation of a target cell population out of a sample of biological specimen by magnetic cell separation followed by flow cytometry or microscopy analysis or a fluorescent based flow sorting for further purification. In this variant the labelling efficiency with X1 and X2 is reduced due to double labelling with the same antigen recognizing moiety.

Embodiment C of the invention is characterized in that in a first step a) at least one first conjugate An-P-Bm-Cq-X1 is provided and after cleaving Cq-X1 from the labelled target moiety in a first step d), the target moiety still labelled with An-P-Bm is labelled with at least one second conjugate Cq-X2 in at least one second step a), wherein the first and second conjugates are provided with different detection moieties X.

In this embodiment, the sample of biological specimens is contacted in step b) with a first conjugate $A_n$-P-$B_m$-$C_q$-$X1_o$, performing the detection in step c), cleaving the conjugate in step d) therefore releasing $C_q$-$X1_o$. The sample of biological specimens still labelled with $A_n$-P-$B_m$ is contacted in a next sequence with $C_q$-$X2_o$, the detection is performed, and the conjugate cleaved in step d) enabling a further sequence or cleaved in subsequent or simultaneous steps d) and e). A, P, B, C are the same kind; n, m, q, o can be the same or different amount. An example for this variant is the magnetic labelling and isolation of a target cell population out of a sample of biological specimen followed by fluorescent labelling enabling flow cytometry or microscopy analysis or a fluorescent based flow sorting for further purification. Compared to embodiment A and B in this variant the labelling efficiency in the second step is not reduced due to readdressing of the same $A_n$-P-$B_m$ of the first sequence.

Embodiment D of the invention is characterized in that steps a) to e) are performed in at least two subsequent sequences, wherein in each sequence conjugates An-P-Bm-Cq-Xo (I) are used having different antigen recognizing moieties A and the same or different detection moieties X.

In this embodiment, the sample of biological specimens is contacted in step b) with a first conjugate $A1_n$-P-$B_m$-$C_q$-$X1_o$, performing the detection in step c), cleaving the conjugate in subsequent or simultaneous steps d) and e). The sample of biological specimens or the isolated fraction of the first sequence is contacted in a next sequence with a second conjugate $A2_n$-P-$B_m$-$C_q$-$X2_o$, the detection is performed, and the conjugate cleaved in subsequent or simultaneous steps d) and e). P, B, C are the same kind; n, m, q, o can be the same or different amount. X1 and X2 is the same or different. A first example for this variant is the sequential magnetic labelling and isolation of two target cell population out of a sample of biological specimen with cell populations recognized by only A1 and only A2. A second example is the magnetic labelling and isolation of a first target cell population and the fluorescent labelling and detection of a second target cell population out of a sample of biological specimen with cell populations recognized by only A1, only A2. A third example for this variant is the magnetic labelling and isolation of a target cell subpopulation recognized by A1+A2 out of a sample of biological specimen with cell populations recognized by only A1, only A2 and A1+A2. Such an isolation strategy is not possible using reversible labelling systems known from literature of the type "$A_n$-$B_m$-$C_q$-$X_o$" with A being a high-affinity antigen recognizing moiety. After the first sequence with those systems the sample of the biological specimen is still labelled with $A1_n$-$B_m$ leading in the second sequence to a double labelling with $A1_n$-$B_m$-$C_q$-$X_o$ and $A2_n$-$B_m$-$C_q$-$X_o$, and to an isolation of all cell populations recognized by only A1, only A2 and A1/A2.

Embodiment E of the invention is characterized in that in step a) at least two conjugates An-P-Bm-Cq-Xo (I) having different antigen recognizing moieties A are provided and in step c) the labelled target moieties are detected via the same detection moiety X.

In this embodiment, the sample of biological specimens is contacted in step b) with a first conjugate $A1_n$-P-$B_m$-$C_q$-$X1_o$ and a second conjugate $A2_n$-P-$B_m$-$C_q$-$X1_o$, performing the detection in step c), cleaving both conjugates in subsequent or simultaneous steps d) and e). P, B, C, X1 are the same kind; n, m, q, o can be the same or different amount. A first example for this variant is the simultaneous magnetic labelling and isolation of two target cell population out of a sample of biological specimen with cell populations recognized by only A1, only A2 or A1+A2. This variant can be extended with further conjugates providing different A. This variant can also be combined with variant C by cleaving the conjugates in step d) therefore releasing $C_q$-$X1_o$. The sample of biological specimens still labelled with $A1_n$-P-$B_m$ respectively $A2n$-P-$B_m$ is contacted in a next sequence with $C_q$-$X2_o$, etc. P, B, C are the same kind; n, m, q, o can be the same or different amount.

Embodiment F of the invention is characterized in that in step a) at least two conjugates An-P-Bm-Cq-Xo (I) having different antigen recognizing moieties A and different enzymatically degradable spacer P are provided and wherein the binding moieties Bm are cleaved from each target moiety labelled by the different conjugates by enzymatically degrading the different spacers P in separate steps e).

In this embodiment, the sample of biological specimens is contacted in step b) with a first conjugate $A1_n$-P1-$B_m$-$C_q$-$X1_o$ and a second conjugate $A2_n$-P2-$B_m$-$C_q$-$X1_o$, performing the detection in step c) cleaving the conjugates in subsequent or simultaneous steps d) and e) wherein step e) is different for P1 and P2. Therefore, a second sequence according to embodiment C can be performed before cleaving step e) for P2. B, C are the same kind; n, m, q, o can be the same or different amount. This variant can be extended with further conjugates. An example for this variant is the simultaneous magnetic labelling and isolation of two target cell population out of a sample of biological specimen with cell populations recognized by only A1, only A2. The sequential release of P1 and P2 enables to cleave first only P1, therefore readdress in a second sequence according to embodiment C with a fluorescent or magnetic label only the cell population still labelled with $A2_n$-P2-$B_m$ with $C_q$-$X2_o$ to finally separate those two cell populations. Compared to embodiment D the process time for this embodiment will be reduced due to existing labelling with $A2_n$-P2-$B_m$ in the second sequence.

Embodiment G of the invention is characterized in that in step a) at least two conjugates An-P-Bm-Cq-Xo (I) having different antigen recognizing moieties A and different first binding moieties B or second binding moieties C are provided, and wherein the fragments Cq-Xo are cleaved from the target moieties labelled by the different conjugates by disrupting the non-covalent bond between Bm and Cq in separate steps d).

In this embodiment, the sample of biological specimens is contacted in step b) with a first conjugate $A1_n$-P-$B1_m$-$C1_q$-$X1_o$ and a second conjugate $A2_n$-P-$B2_m$-$C2_q$-$X1_o$, performing the detection in step c), cleaving the conjugates in subsequent or simultaneous steps d) and e) wherein step d) is different for B1-C1 and B2-C2. P, X are the same kind; n, m, q, o can be the same or different amount. This variant can be extended with further conjugates. An example for this variant is the simultaneous magnetic labelling and isolation of two target cell population out of a sample of biological specimen with cell populations recognized by only A1, only A2. The sequential release of $C1_q$-$X1_o$ and $C2_q$-$X1_o$ enables a further detection step in-between after release of $C1_q$-$X1_o$ to separate those two cell populations which can finally be cleaved by the same mechanism in step e). Compared to embodiment D and F the process time for this embodiment will be even further reduced. The embodiment can be combined with embodiment C.

Embodiment H of the invention is characterized in that in step a) at least two conjugates An-P-Bm-Cq-Xo (I) having different antigen recognizing moieties A, different detection moieties X and different first binding moieties B or second binding moieties C are provided, and wherein the fragments Cq-Xo are cleaved from the target moieties labelled by the different conjugates by disrupting the non-covalent bond between Bm and Cq in separate steps d).

In this embodiment, the sample of biological specimens is contacted in step b) with a first conjugate $A1_n$-P-$B1_m$-$C1_q$-$X1_o$ and a second conjugate $A2_n$-P-$B2_m$-$C2_q$-$X2_o$, performing the detection simultaneously or in two subsequent steps c), the conjugates in subsequent or simultaneous steps d) and e) wherein step d) is different for B1-C1 and B2-C2. P are the same kind; n, m, q, o can be the same or different amount. An example for this variant is the fluorescent labelling with two parameters and two fluorescent dye and isolation of a target cell subpopulation out of a sample of biological specimen with cell populations recognized by only A1, only A2 and A1+A2. The different $C1_q$-$X1_o$ and $C2_q$-$X2_o$ enable a specific labelling and the release can be performed simultaneously or sequentially in different step d) and e). This variant can be extended with further conjugates providing different A and X, e.g., for multiple parameter fluorescent labelling, detection, isolation and release of cell subpopulations. This variant can also be combined with variant C.

Embodiment I of the invention is characterized in that in step a) at least two conjugates An-P-Bm-Cq-Xo (I) having different antigen recognizing moieties A, different enzymatically degradable spacer P, different first binding moieties B or second binding moieties C and different detection moieties X are provided.

In this embodiment, the sample of biological specimens is contacted in step b) with a first conjugate $A1_n$-P1-$B1_m$-$C1_q$-$X1_o$ and a second conjugate $A2_n$-P2-$B2_m$-$C2_q$-$X2_o$, performing the detection simultaneously or in two subsequent steps c), cleaving the conjugates in subsequent or simultaneous steps d) and e). n, m, q, o can be the same or different amount. This variant can be extended with further conjugates. This variant can also be combined with variant C. This embodiment enables a plurality of possibilities to sequentially or simultaneously label, separate and release at least two target cell population out of a sample of biological specimen.

The method of the invention, especially the above described embodiments may be performed with at least one conjugate of An-P-Bm-Cq-Xo (I) and at least one additional conjugate of $A_n$-P'-$B'_m$-$C'_q$-$X_o$ (II) and/or $A_n$-$B_m$-$C_q$-$X_o$ (III) and/or $A_n$-P-$X_o$ (IV) and/or $A_n$-$X_o$ (V). Those additional conjugates (II)-(V) survive at least one of the cleaving steps d) and or e). Therefore, the method of the invention can be performed in the following embodiments:

Embodiment J of the invention is characterized in that in step a) at least one conjugate An-P-Bm-Cq-Xo (I) and at least one conjugate A-$X_o$ (V) having different antigen recognizing moieties A are provided.

In this embodiment, the sample of biological specimens is contacted in step b) with a first conjugate $A1_n$-P-$B_m$-$C_q$-$X1_o$ and a second conjugate A2-$X1_o$, performing the detection in step c) cleaving the conjugate $A1_n$-P-$B_m$-$C_q$-$X1_o$ in subsequent or simultaneous steps d) and e). $A2_n$-$X1_o$ survives the steps d) and e). X1 is the same kind; n, m, q, o can be the same or different amount. This variant can be extended with further conjugates. An example for this variant is the simultaneous magnetic labelling and isolation of two target cell population out of a sample of biological specimen with cell populations recognized by only A1, only A2. The sequential release of $C1_q$-$X1_o$ enables a further detection step after release of $C1_q$-$X1_o$ to separate those two cell populations.

Only the cell population targeted by A1 can finally be cleaved in step e). The cell population targeted by A2 is non-reversible labelled with $A2n$-$X1_o$. The embodiment can be combined with embodiment C.

Embodiment K of the invention is characterized in that in step a) at least one conjugate An-P-Bm-Cq-Xo (I) and at least one conjugate $A_n$-$X_o$ (V) having different antigen recognizing moieties A and different detection moieties X are provided.

In this embodiment, the sample of biological specimens is contacted in step b) with a first conjugate $A1_n$-P-$B_m$-$C_q$-$X1_o$ and a second conjugate A2-$X2_o$, performing the detection simultaneously or in two subsequent steps c) cleaving the conjugate $A1_n$-P-$B_m$-$C_q$-$X1_o$ in subsequent or simultaneous steps d) and e). $A2_n$-$X2_o$ survives the steps d) and e). n, m, q, o can be the same or different amount. This variant can be extended with further conjugates. An example for this variant is the fluorescent labelling with two parameters and two fluorescent dye, wherein one labelling is non-reversible and the second reversible. This variant can be extended with further conjugates providing different A and X, e.g., for multiple parameter fluorescent labelling, detection, isolation and release of cell subpopulations. This variant can also be combined with variant C.

Embodiment L of the invention is characterized in that in step a) at least one conjugate An-P-Bm-Cq-Xo (I) and at least one conjugate $A_n$-P-$X_o$ (IV) having different antigen recognizing moieties A are provided.

In this embodiment, the sample of biological specimens is contacted in step b) with a first conjugate $A1n$-P-$B_m$-$C_q$-$X1_o$ and a second conjugate A2-P-$X2_o$, performing the detection simultaneously or in two subsequent steps c) cleaving the conjugate $A1_n$-P-$B_m$-$C_q$-$X1_o$ in step d). $A2_n$-P-$X2_o$ survives the step d), but is released simultaneously to $A1_n$-P-$B_m$ in step e). X1 and X2 are the same or different kind, P is the same kind; n, m, q, o can be the same or different amount. This variant can be extended with further conjugates. An example for this variant is the simultaneous magnetic labelling and isolation of two target cell population out of a sample of biological specimen with cell populations recognized by only A1, only A2. The sequential release of $C1_q$-$X1_o$ enables a further detection step after release of $C1_q$-$X1_o$ to separate those two cell populations which can finally be cleaved by the same mechanism in step e). This variant can also be combined with variant C.

Embodiment M of the invention is characterized in that in step a) at least one conjugate An-P-Bm-Cq-Xo (I) and at least one conjugate $A_n$-P-$X_o$ (IV) having different antigen recognizing moieties A and different enzymatically degradable spacers P are provided.

In this embodiment, the sample of biological specimens is contacted in step b) with a first conjugate $A1_n$-P1-$B_m$-$C_q$-$X1_o$ and a second conjugate $A2_n$-P2-$X2_o$, performing the detection simultaneously or in two subsequent steps c), cleaving the conjugates in subsequent or simultaneous steps d) and e) wherein step e) is different for P1 and P2. $A2_n$-P2-$X2_o$ survives the step e) for P1. X1 and X2 are the same or different kind; n, m, q, o can be the same or different amount. An example for this variant is the simultaneous magnetic labelling and isolation of two target cell population out of a sample of biological specimen with cell populations recognized by only A1, only A2. The sequential release of $C1_q$-$X1_o$ enables a further detection step after release of $C1_q$-$X1_o$ to separate those two cell populations which can finally be cleaved by different mechanism in step e). This variant can also be combined with variant C.

Embodiment N of the invention is characterized in that in step a) at least one conjugate An-P-Bm-Cq-Xo (I) and at least one conjugate An-Bm-Cq-Xo (III) having different antigen recognizing moieties A and different detection moieties X are provided.

In this embodiment, the sample of biological specimens is contacted in step b) with a first conjugate $A1_n$-P-$B1_m$-$C1_q$-$X1_o$ and a second conjugate A2n-B2m-C2q-$X2_o$ (III), performing the detection simultaneously or in two subsequent steps c), cleaving the conjugates in subsequent or simultaneous steps d) and e) wherein step d) is different for B1-C1 and B2-C2 and the cell population targeted by A1 can finally be cleaved in step e). X1 and X2 are the same or different kind; n, m, q, o can be the same or different amount. The sequential release of $C1_q$-$X1_o$ and $C2_q$-$X2_o$ enables a further detection step in-between after release of $C1_q$-$X1_o$ to separate those two cell populations. The embodiment can be combined with embodiment C.

Use of the Method

The method of the invention can be used for various applications in research, diagnostics and cell therapy.

In a first use of the invention, biological specimens like cells are detected or isolated for counting purposes i.e. to establish the amount of cells from a sample having a certain set of antigens recognized by the antigen recognizing moieties of the conjugate.

In a second use, one or more populations of biological specimens are separated for purification of target cells. Those isolated purified cells can be used in a plurality of downstream applications like molecular diagnostics, cell cultivation, or immunotherapy.

In other uses of the invention, the location of the target moieties like antigens on the biological specimens recognized by the antigen recognizing moieties of the conjugate is determined. Advanced imaging methods are known as "Multi Epitope Ligand Cartography", "Chip-based Cytometry" or "Multioymx" and are described, for example, in EP 0810428, EP1181525, EP 1136822 or EP1224472. In this technology, samples of biological specimen are contacted in sequential cycles with antigen recognizing moieties coupled to a detection moiety, the location of the antigen is detected by the detection moiety and the detection moiety is afterwards eliminated. Therefore, subsequent cycle of labelling-detection-elimination provide the possibility to map protein networks, localize different cell types or the analysis of disease-related changes in the proteome.

EXAMPLES

Example 1—Conjugation of Antibody- or Fab-Dextran-PEO-Biotin

To prepare antibody- or Fab-dextran-PEO-Biotin-conjugates with PEO-Biotin amino dextran was incubated with NHS-activated PEO-Biotin (e.g., NHS-$PEG_4$-Biotin, available from Thermo Scientific/Pierce). After 60 min incubation time at room temperature, the dextran-PEO-Biotin-conjugate was purified by size exclusion chromatography utilizing PBS/EDTA-buffer. The dextran-PEO-Biotin-conjugate was further activated by incubation with SMCC for 60 min at room temperature and purified by size exclusion chromatography utilizing PBS/EDTA-buffer. Antibody or Fab was reduced with 10 mM DTT in MES-buffer. After 60 min incubation time at room temperature, the antibody or Fab was purified by size exclusion chromatography utilizing PBS/EDTA-buffer. For the conjugation of the antibody- or Fab-dextran-PEO-Biotin-conjugate activated Fab or antibody was added to the activated dextran-PEO-Biotin. After 60 min incubation time at room temperature, β-mercaptoethanol followed by N-ethylmaleimide were added with a molar excess to block unreacted maleimide- or thiol-functional groups. The antibody- or Fab-dextran-PEO-Biotin-conjugate was purified by size exclusion chromatography utilizing PBS/EDTA-buffer. The concentrations of antibody or Fab were determined by the absorbance at 280 nm and absorbance.

Example 2—Conjugation of Antibody- or Fab-PEO-Biotin for Comparison to Antibody- or Fab-Dextran-PEO-Biotin To prepare antibody- or Fab-PEO-Biotin-conjugates antibody or Fab was reduced with 10 mM DTT in MES-buffer. After 60 min incubation time at room temperature, the antibody or Fab was purified by size exclusion chromatography utilizing PBS/EDTA-buffer. For the conjugation of the antibody- or Fab-dextran-PEO-Biotin-conjugate activated Fab or antibody was incubated with a molar excess of thiol-reactive maleimide-PEO-Biotin (e.g., maleimide-$PEG_2$-Biotin, available from Thermo Scientific/Pierce). After 15 h incubation time at room temperature, the antibody- or Fab-PEO-Biotin-conjugate was purified by size exclusion chromatography utilizing PBS/EDTA-buffer. The concentrations of antibody or Fab were determined by the absorbance at 280 nm and absorbance.

Example 3—Cell Surface Labelling with Fab-Dextran-PEO-Biotin/Anti-Biotin-APC (According to the Invention) Vs. Fab-PEO-Biotin/Anti-Biotin-APC Cell surface staining procedure 1) "with washing step": PBMCs in PBS/EDTA/BSA-buffer were first labelled with 2.0 µg/mL anti-CD8-Fab-dextran-PEO-Biotin or anti-CD8-Fab-PEO-Biotin for 5 min at 4° C. The cells were washed with cold PBS/EDTA-BSA-buffer and second labelled in PBS/EDTA/BSA-buffer with a 2-fold molar excess anti-Biotin-APC (molar ratio Fab:anti-Biotin=1:2) (available from Miltenyi Biotec GmbH) for 10 min at 4° C. The cells were washed with cold PBS/EDTA-BSA-buffer and analysed by flow cytometry.

Cell surface staining procedure 2) "w/o washing step": PBMCs in PBS/EDTA/BSA-buffer were first labelled with 2.0 µg/mL anti-CD8-Fab-dextran-PEO-Biotin or anti-CD8-Fab-PEO-Biotin for 5 min at 4° C. Afterwards the cells were immediately second labelled in PBS/EDTA/BSA-buffer with a 2-fold molar excess anti-Biotin-APC (molar ratio Fab:anti-Biotin=1:2) (available from Miltenyi Biotec GmbH) for 10 min at 4° C. The cells were washed with cold PBS/EDTA-BSA-buffer and analysed by flow cytometry.

Figure 2:
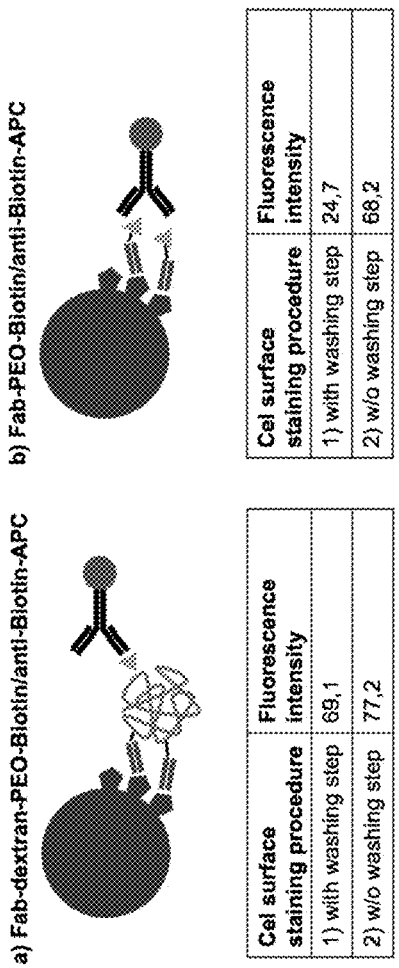
FIG. 2 shows exemplary results of flow cytometry analysis of cell surface labelling with Fab-dextran-PEO-Biotin/anti-Biotin-APC (a) (according to the invention) vs. Fab-PEO-Biotin/anti-Biotin-APC (b) (for comparison)

FIG. 2 shows exemplary results of flow cytometry analysis of cell surface labelling with Fab-dextran-PEO-Biotin/anti-Biotin-APC (a) (according to the invention) vs. Fab-PEO-Biotin/anti-Biotin-APC (b) (for comparison).

PBMCs were labelled subsequently by first incubating anti-CD8-Fab-dextran-PEO-Biotin respectively anti-CD8-Fab-PEO-Biotin and second incubating anti-Biotin-APC. Labelling procedure 2) w/o a washing step revealed a comparable fluorescence intensity of 77.2 respectively 68.2. The anti-CD8-Fab-dextran-PEO-Biotin conjugate consists of two Fabs which are covalently multimerized via dextran-PEO-Biotin. Anti-CD8-Fab-PEO-Biotin is a monomeric conjugate which can be dimerized by binding to anti-Biotin- APC. Therefore, labelling procedure 1) with a washing step in-between the first and second incubation furnished a reduced fluorescence intensity (24.7) using anti-CD8-Fab-PEO-Biotin/anti-Biotin-APC due to the fast dissociation characteristic of the low-affinity monomeric anti-CD8-Fab-PEO-Biotin (b). In contrast the first labelling with the multimerized anti-CD8-Fab-dextran-PEO-Biotin is stable during the washing step and the resulting fluorescence intensity comparable to the value reached with labelling procedure 2) w/o washing step (a). This washing step is beneficial to remove unbound Fab-conjugate to reduce the risk of unspecific binding.

Example 4—Reversible Cell Labelling with Fab-Dextran-PEO-Biotin/Anti-Biotin-APC (According to the Invention)

PBMCs in PBS/EDTA/BSA-buffer were first labelled with 0.25 µg/mL anti-CD8-Fab-dextran-PEO-Biotin for 5 min at 4° C. Afterwards the cells were immediately second labelled in PBS/EDTA/BSA-buffer with anti-Biotin-Microbeads (available from Miltenyi Biotec GmbH) for 15 min at 4° C. and with anti-CD8-PE for 5 min at 4° C. The cells were washed with cold PBS/EDTA/BSA-buffer and resuspended in 500 µL cold buffer. The suspension was applied on a MS-column (available from Miltenyi Biotec GmbH) and a magnetic field for magnetic cell separation. The enriched cells were washed within the magnetic field and the column was removed from the separator prior to the elution of the cells with 1 mL of cold PBS/EDTA/BSA-buffer. An aliquot of this enriched fraction was separated and stained with anti-Dextran-APC for flow cytometry analysis. The residual enriched fraction was splitted and one part incubated with 2 mM biotin for 10 min at 21° C. The other part was incubated with 2 mM biotin and dextranase for 10 min at 21° C. The cell suspension was applied onto a second column and the flow-through was collected as eluted cells. An aliquot of this eluted fractions was separated and stained with anti-Dextran-APC for flow cytometry analysis. The aliquot of the enriched or eluted fractions were incubated with anti-Dextran-APC (available from Miltenyi Biotec GmbH) for 10 min at 4° C. The cells were washed with cold PBS/EDTA-BSA-buffer and analysed by flow cytometry.

Figure 3:
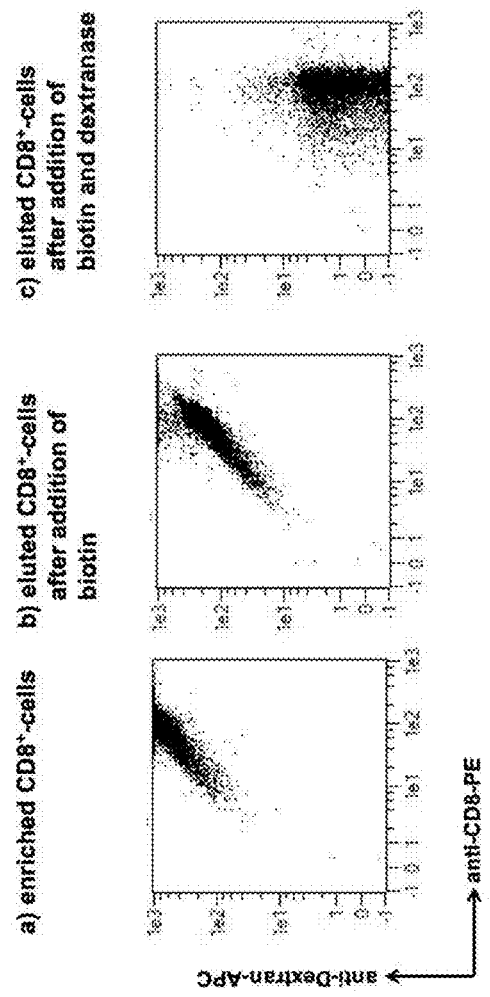
FIG. 3 shows exemplary dot plots of the result of flow cytometry analysis of reversible cell labelling with Fab-dextran-PEO-Biotin/anti-Biotin-MicroBeads.

FIG. 3 shows exemplary dot plots of the result of flow cytometry analysis of reversible cell labelling with Fab-dextran-PEO-Biotin/anti-Biotin-MicroBeads.

PBMCs were labelled subsequently by first incubating anti-CD8-Fab-dextran-PEO-Biotin and second incubating anti-Biotin-MicroBeads. The magnetically labelled CD8+ target cells were isolated in a magnetic field. The enriched cells were analysed by labelling with anti-Dextran-APC. This antibody recognizes the dextran of the anti-CD8-Fab-dextran-PEO-Biotin and of the anti-Biotin-MicroBeads. Therefore, the enriched cells revealed a high fluorescence intensity for APC (a). After the addition of the competing molecule biotin the anti-Biotin-MicroBeads were released from the target cells and the cells were not retained anymore in the magnetic field. The anti-CD8-Fab-dextran-PEO-Biotin conjugate consists of two Fabs which are covalently multimerized via dextran-PEO-Biotin and therefore remained on the cell surface. Flow cytometry analysis after anti-Dextran-APC labelling revealed a reduced fluorescence intensity of APC compared to the enriched fraction due to the absence of the anti-Biotin-MicroBeads and the remaining anti-CD8-Fab-dextran-PEO-Biotin (b). After the addition of the competing molecule biotin and the dextran-degrading enzyme Dextranase anti-Biotin-MicroBeads were released and the anti-CD8-Fab-dextran-PEO-Biotin degraded resulting in a monomerization of the anti-CD8-Fab. Flow cytometry analysis after anti-Dextran-APC labelling furnished a fluorescence intensity of APC in the range of the detection limit due to the absence of the anti-Biotin-Micro-Beads and anti-CD8-Fab-dextran-PEO-Biotin (c).

What is claimed is:

1. A method for detecting a target moiety in a sample of biological specimens by:
    a) providing at least one conjugate with the general formula (I)

$$A_n\text{-}P\text{-}B_m\text{-}C_q\text{-}X_o \qquad (I)$$

wherein
        A: is an antigen recognizing moiety A;
        P: is an enzymatically degradable spacer;
        B: is a first binding moiety;
        C is a second binding moiety;
        X: is a detection moiety;
        n is an integer greater than 1 and less than 100;
        m, q, o are integers between 1 and 100, and
        wherein B and C are non-covalently bound to each other and A and B are covalently bound to P, and wherein the antigen recognizing moiety A is a Fab fragment of an antibody against an antigen and wherein the enzymatically degradable spacer is a polysaccharide;
    b) labelling the target moiety recognized by the antigen recognizing moiety A with the at least one conjugate with the general formula (I);
    c) detecting the labelled target moiety via detecting moiety $X_o$;
    d) cleaving $C_q\text{-}X_o$ by disrupting the non-covalent bond between $B_m$ and $C_q$ from the labelled target moiety; and
    e) cleaving the binding moiety $B_m$ from the labelled target moiety by enzymatically degrading spacer P thereby removing A, B, C, P, X form the target moiety.

2. The method according to claim 1, characterized that disrupting the non-covalent bond between $B_m$ and $C_q$ in step d) is performed by adding a release agent that binds to the first binding moiety B, thereby displacing the second binding moiety C and/or by adding a release agent that binds to the second binding moiety C, thereby displacing the first binding moiety B.

3. The method according to claim 1, characterized in that step d) and e) are performed simultaneously.

* * * * *